United States Patent [19]

Dhaon

[11] Patent Number: 5,698,676

[45] Date of Patent: Dec. 16, 1997

[54] USE OF PROPYLENE OXIDE AS AN ACID SCAVENGER IN PEPTIDE SYNTHESIS

[75] Inventor: Madhup K. Dhaon, Mundelein, Ill.

[73] Assignee: Abbott Laboratories, Abbott Park, Ill.

[21] Appl. No.: 565,465

[22] Filed: Nov. 30, 1995

[51] Int. Cl.$^6$ .............. A61K 38/00; C07K 5/00; C07K 7/00; C07K 16/00

[52] U.S. Cl. .............. 530/334; 530/333; 530/335; 530/337; 530/338

[58] Field of Search .................... 530/333, 334, 530/335, 337, 338

Primary Examiner—Cecilia J. Tsang
Assistant Examiner—Jennifer Harle
Attorney, Agent, or Firm—Michael J. Ward

[57] ABSTRACT

A process of synthesizing a peptide using an alkylene oxide as an acid scavenger is provided. A process of the present invention can be used in a solid phase or solution phase synthetic process where peptide synthesis occurs by the sequential addition of N-α-amino-Boc-protected residues followed by acid deprotection of that N-α-amino protecting group and scavenging of the acid.

9 Claims, No Drawings

1

USE OF PROPYLENE OXIDE AS AN ACID SCAVENGER IN PEPTIDE SYNTHESIS

TECHNICAL FIELD OF THE INVENTION

The field of the invention is peptide synthesis. More particularly, the present invention pertains to the use of an alkylene oxide as an acid scavenger in solid or solution phase peptide synthesis.

BACKGROUND OF THE INVENTION

The preparation of synthetic peptides can proceed in either a solid or solution phase depending on whether the peptide is bound to a solid support such as a resin or its C-terminus end is protected, e.g., by an ester or an amide. In both cases, synthesis typically proceeds from the carboxyl (C)- to the amino (N)-terminus by the sequential addition of activated, N-α-amino-protected amino acid residues to N-α-amino-unprotected residues.

In accordance with such typical, existing methods, synthesis begins with the C-terminal amino acid residue, which residue is protected at its α-amino group and which residue is either linked to a solid support via its α-carboxyl group (solid phase) or protected at its α-carboxyl with an ester or amide (solution phase). The peptide chain is built by deprotecting the C-terminal residue (removing the protecting group from the α-amino group), adding an activated, N-α-amino-protected residue, and repeating this process until the peptide chain is complete. The completed chain is then cleaved from the solid support (solid phase), deprotected at all positions and recovered. The unrequired protecting groups can be removed by several deprotecting conditions known to those skilled in the art.

It can be seen that an essential step in peptide synthesis is the deprotection or removal of the N-α-amino protecting group from residues after they are added to the peptide chain. The N-α-amino protecting group of choice in existing peptide synthetic methods is a tert-butoxycarbonyl group (Boc).

In existing methods, the Boc protecting group is removed by exposing the Boc-protected residue on the chain to a strong acid. Typical reagents of choice for deprotection in existing methods are trifluoroacetic acid (TFA) in a halogenated solvent, such as dichloromethane (DCM), hydrochloric acid (HCl) in dioxane ($C_4O_2H_8$), sulfuric acid ($H_2SO_4$) in dioxane, or methanesulfonic acid ($CH_4SO_3$) in dioxane. The acid used to remove the Boc protecting group is typically neutralized with a tertiary amine (t-base) such as N-methylmorpholine (NMM), triethylamine (TEA) or N-diisopropylethylamine (DIEA).

The use of t-bases in peptide synthesis is associated with problems concerning product integrity. Those t-bases give rise to counter ion species under equilibrium conditions leading to side reactions such as racemization and α/β rearrangements in aspartic acid containing peptides, which side reactions give rise to undesirable product structure.

There continues to be a need to provide a new method of deprotecting peptides during peptide synthesis that avoids the use of t-bases and the attendant possible side reactions.

BRIEF SUMMARY OF THE INVENTION

The present invention provides a peptide synthetic process that uses an alkylene oxide as an acid scavenger (acid neutralizer). In accordance with a process of the present invention, a strong acid can be used for the removal of Boc protecting groups from the growing peptide chain and the resultant acid bound to the peptide chain is scavenged with the alkylene oxide to generate free amine and chloropropanols.

The free amine is then available for reaction with the next N-α-amino-Boc protected residue to produce the new peptide. An alkylene oxide can be used as an acid scavenger in peptide synthetic schemes involving either solid or solution phase procedures. A preferred alkylene oxide is propylene oxide.

DETAILED DESCRIPTION OF THE INVENTION

The present invention provides a process of synthesizing a peptide. The synthetic process includes the steps of reacting an N-α-amino-Boc-protected amino acid residue with an N-α-amino deprotected amino acid residue to form a peptide having an α-amino-Boc-protected amino terminus, reacting the peptide with an acid to remove the α-amino-Boc protecting group from the amino terminus, and neutralizing the acid with an alkylene oxide.

The N-α-amino unprotected amino acid residue used in the synthetic process is a single amino acid residue or the N-terminal residue of a partially built peptide chain. That amino acid residue can exist in a solid or solution phase in accordance with standard techniques. Where the peptide exists in a solid phase, that peptide is either directly affixed to a solid support such as a resin or is linked via an amide bond to one or more residues affixed to the support.

Means of affixing amino acid residues to a solid support for peptide synthesis are well known in the art. The residue is affixed to the solid support via the C-terminus carboxyl group of that residue. Typically, attachment of the amino acid(s) to the support is accomplished using an N-α-amino-Boc-protected residue. After attachment of the amino acid(s), the N-α-amino-Boc protecting group is removed to provide the unprotected residue or peptide chain.

The same steps can be used where the peptide is being synthesized in solution. In solution phase synthesis, however, none of the residues are affixed to a solid support. The α-carboxyl group of the C-terminal residue is protected to prevent amide bond formation at this position. Suitable protecting groups for this carboxyl group are well known in the art and include such groups as methyl, butyl, benzyl esters, or amides and the like.

Peptide synthesis proceeds in solution by the sequential addition of N-α-amino-Boc protected amino acids to either a single N-α-amino unprotected, C-α-carboxyl-protected residue or to the N-terminal residue of a partially assembled peptide chain where the peptide chain is C-α-carboxyl-protected and N-α-amino-unprotected.

The N-α-amino-Boc protected amino acids used to add to the peptide chain being synthesized are readily available from commercial sources (e.g., Sigma Chem. Co., St. Louis, Mo.). Those N-α-amino-Boc protected amino acids have unprotected α-carboxyl groups, which groups react with the unprotected N-α-amino groups of existing chain residues to form an amide or peptide bond and thus extend the peptide chain in the N-terminal direction.

It can thus be seen that peptide synthesis proceeds in the C-terminal to N-terminal direction by the sequential steps of deprotecting the N-α-amino group of residues in the chain with acid, neutralizing the acid, and adding N-α-amino-Boc protected, α-carboxyl-unprotected amino acids to form an amide bond and extend the chain. In contrast to existing methods, the present invention uses an alkylene oxide instead of a t-base to neutralize acid during deprotection. The use of t-bases as acid scavengers may be eliminated.

Alkylene oxides are used as an acid scavenger. A preferred alkylene oxide is propylene oxide. The propylene oxide is preferably contained in a solvent, such as DCM or dimethylformamide (DMF). The time required for neutralization with propylene oxide may be longer than the time required using t-bases. One of ordinary skill in the art can readily determine appropriate times to ensure neutralization. Where propylene oxide was used to neutralize HCl in a solid phase, the resin was treated 3–4 times with propylene oxide for an extended period of time (total 1–4 hours). After extended neutralization of the resin bound acid, subsequent additions were found to proceed efficiently and rapidly. Reaction side-products obtained with the use of propylene oxide are 1- and 2-chloropropanols, which side-products do not interfere with peptide synthesis.

Typically, in peptide synthesis, propylene oxide can be used to neutralize the acid in a solvent, such as a halogenated solvent, DMF, THF, and N-methyl-pyrrolidone (NMP). A process of the present invention preferably uses HCl in the solvent tetrahydrofuran (THF). The use of THF/HCl in the assembly process may also avoid the neutralization that may be necessary in TFA/DCM processes.

The THF/HCl generated from the cleavage of Boc-group can be collected separately and the excess HCl blown under nitrogen and this waste then combined with DMF waste. Because the THF/HCl solution (4N) may decompose over long periods of time (e.g., 1–2 weeks), this solution is preferably freshly prepared each day.

A detailed description of the use of a synthetic process of the present invention in the solid- and solution-phase synthesis of peptides is set forth hereinafter in the Examples. The following Examples illustrate only preferred embodiments of the present invention and are not limiting of the specification and claims in any way.

EXAMPLE 1: Solid Phase Peptide Synthesis

The peptide, 5 Leu-Enkephalin was synthesized using the general procedure outlined below.

A resin was treated twice with 4N HCl/THF. The first treatment was for 5 minutes and the second treatment for 30 minutes. The resin was then washed three times with a solvent, such as THF or DCM. Each wash took 2 minutes. The resin was then washed again with DCM or DMF.

The washed resin was treated twice with a 20% solution of propylene oxide in solvent (DCM or DMF). The first treatment took 30 minutes and the second treatment took 60 minutes. The treated resin was washed again (3X) with the propylene oxide solvent (DCM or DMF). Each wash took 2 minutes.

The resin was then coupled to an N-α-amino-Boc-protected amino acid residue in DCM or DMF using DIC/HOBt for 2–12 hours. The Boc-protecting group was removed by acid treatment. The deprotected amino acid on the resin was then treated with a 20% solution of propylene oxide in solvent (DCM or DMF) for 30 minutes and washed (2X) with solvent (2 minutes for each wash).

If necessary, recoupling of the N-α-amino-Boc-protected amino acid residue was performed for an additional 2–6 hours. Finally, the resin was washed (3X) for 2 minutes each with THF. These steps were then repeated for each amino acid residue until the peptide assembly was complete.

In a first assembly, synthesis started on a Boc-Leu-Merrifield Resin (Bachem Chemicals, Torrance Calif.). The amino acids were coupled in the order of Boc-L-Phe (N-tert-butyloxycarbonyl-L-phenylalanine), Boc-Gly (N-tert-butyloxycarbonyl glycine), Boc-Gly and Boc L-Tyr (2-Br-Z)(N-tert butyloxycarbonyl-0-(2-bromobenzyloxycarbonyl) -L-tyrosine. In this first assembly, HCl in THF was used as the acid for deprotection, DCM and DMF were used as the solvents, and propylene oxide in DCM was used as the acid scavenger.

After assembly was complete, the peptide was cleaved from the resin using HF/anisole. The crude peptide was extracted from the resin with 20% acetic acid, and then lyophilized. The lyophilized crude peptide was shown to be 85% pure by HPLC, and further identified by mass and amino acid analysis (AAA).

In a second assembly, the synthesis of the peptide proceeded as in the first assembly except that HCl in THF was used as the acid during deprotection, THF and DMF were used as the solvents, and propylene oxide in THF was used as the acid scavenger. The peptide was cleaved from the resin using HF/anisole. The crude peptide had a purity of 86%, and was further characterized by mass spectroscopy. This synthetic assembly demonstrates that the acid (TFA) normally used in the peptide synthesis in a dichloromethane (DCM) solution, followed by DCM washes can be totally eliminated from the assembly procedure. Therefore, one may eliminate the use of halogenated reagents/solvents in the process.

In a third assembly, TFA was used to deprotect the Boc-group on the resin instead of HCl. The trifluoroacetate salt on the resin was neutralized by propylene oxide in DCM and DCM and DMF were used as the solvents. The product was found to be 81% pure by HPLC.

In a fourth assembly, the peptide was synthesized using DMF and THF as the solvents, HCl in THF as the acid during deprotection, and 10% DIEA in DMF as the acid scavenger. The peptide was cleaved from the resin using HF/anisole. The assembly of the peptide proceeded extremely well when THF/HCl was used as a Boc-cleaving agent and 10% DIEA used as the acid scavenger. The neutralization was done in 5 minutes and all the couplings were in the range of 99.8%–99.9%. DMF was only used as a solvent in washing and couplings. The crude peptide was 84% pure by HPLC.

EXAMPLE 2: Solution Phase Synthesis

These studies show the use of propylene oxide as an acid scavenger in a solution phase peptide synthesis. In a normal protocol, an activated derivative of a protected amino acid is coupled to an N-α-amino-deprotected amino acid hydrochloride or N-α-amino-deprotected peptide hydrochloride salt in the presence of a t-base like N-methylmorpholine (NMM) or triethylamine (TEA) or N-diisopropylethyl amine (DIEA) to form the new amide bond and generate a new peptide. The presence of a t-base could affect the integrity of the product formed due to the racemization of the activated amino acid derivative. The replacement of t-base by propylene oxide keeps the reaction medium neutral and generates the unreactive species, 2-chloropropanol and 1-chloro-2-propanol.

Added amino acids can be activated by the use of several activating agents like carbodiimides, mixed anhydrides, BOP-Cl, BOP reagents and the like. Those activating agents are dissolved in solvents such as tetrahydrofuran, ethyl acetate, methylene chloride, and the like. In the studies reported herein, the protected amino acid derivatives were activated by the use of 1-ethyl-3-dimethyl aminopropyl carbodiimide hydrochloride (EDAC) and 1-methylmorpholine in tetrahydrofuran/methylene chloride as solvents. The yield of the reactions were in the range of 50–90%.

Six different peptides were synthesized using the above described procedures with propylene oxide as the acid scavenger.

A. Boc-Leu-Gly-OMe:

Boc-Leucine monohydrate (5.0 g, 20 mM) and 1-hydroxybenzotriazole (HOBt, 2.8 g, 22 mM) were dissolved in tetrahydrofuran (THF, 60 ml) and the solution was cooled to 0°–5° C. under an ice bath. 1-Ethyl-3-(3-dimethylaminopropyl)-carbodiimide hydrochloride (EDAC, 4.22 g, 22 mM) was added and the reaction stirred under ice bath for 15–30 minutes. Glycine methyl ester hydrochloride (2.8 g, 22 mM) was added followed by the addition of a solution of propylene oxide (1.53 ml, 22 mM) in THF. The reaction mixture was stirred under ice for 2–3 hours and at room temperature for 12–18 hours.

0.5N hydrochloric acid (5–25 ml) and water (50 ml) were added to the reaction mixture. The mixture was concentrated and the oil extracted with ethyl acetate (100 ml). The organic solution was washed with 0.5N HCl, 5% bicarbonate (100 ml), a sodium chloride solution (100 ml), dried with anhydrous sodium sulfate and concentrated. The crude product obtained was crystallized from ethyl acetate/heptane to give the dipeptide in a yield of 4.6 g (75%). The melting point (mp) was 130°–131° C. NMR and mass spectral data were consistent with the structure.

B. Boc-Phe-Leu-Gly-OMe

Boc-Leu-Gly-OMe (1.5 g, 4.7 mM), prepared using the procedures described above, was deprotected at the N-terminus by HCl/EtOAc solution for 1 hour. The solvent was removed, and the residue treated with ether and concentrated. The residue was dissolved in THF (10 ml).

The activated ester of Boc-Phe (1.4 g, 5.2 mM) was generated from HOBt (0.8 g, 5.2 mM) in THF (15 ml) as described above. The solution of HCl. Leu-Gly-OMe in THF was added followed by the addition of propylene oxide (0.38 ml, 5.5 mM). Crystallization from ethyl acetate/heptane gave 1.0 g (50%) of tripeptide, mp 163°–164° C. NMR and mass spectral data were consistent with the structure.

C. Z-Phe-Gly-OBut:

Carbobenzoxy phenylalanine (Z-Phe)(6.0 g., 20 mM) and 1-hydroxybenzotriazole (HOBt, 3.21 g, 21 mM) were dissolved in tetrahydrofuran (THF, 80 ml) and dichloromethane (DCM, 20 mM) and the solution was cooled to 0°–5° C. under an ice bath. 1-Ethyl-3-(3-dimethylaminopropyl)-carbodiimide hydrochloride (EDAC, 4.22, 22 mM) was added, and the reaction stirred under ice bath for 15–30 minutes. Glycine tert-butylester hydrochloride (3.52g, 21 mM) was added to the solution, followed by the addition of a solution of propylene oxide (1.75 ml, 25 mM) in THF. The reaction mixture was stirred under ice bath for 2–3 hours and at room temperature for 12–18 hours.

0.5N hydrochloric acid (30 ml) was added to the reaction mixture and the resulting mixture was concentrated. The residue was extracted with ethyl acetate (120 ml). The organic solution was washed with 0.5N HCl, 5% bicarbonate (100 ml) and a sodium chloride solution (100 ml), dried with anhydrous sodium sulfate and concentrated. The crude peptide obtained was crystallized from ethyl acetate/heptane to give the dipeptide, with a yield of 7.8 g (95%) and having amp of 87°–88° C. NMR and mass spectral data were consistent with the structure.

D. Boc-Phe-D-Ala-OMe

The activated ester of Boc-Phe (5.09 g, 18.85 mM) was generated from HOBt (3.0 g, 20 mM) in THF (70 ml) as described above. To this activated ester, D-Ala-Ome HCl (2.8 g, 20 mM) and a solution of propylene oxide (1.7 ml, 24 mM) in THF were sequentially added. DCM (20 ml) was then added. Crystallization from ethyl acetate/heptane gave 5.4 g (81%) of dipeptide. NMR and mass spectral data were consistent with the structure.

E. Boc-Ala-Leu-OMe:

This dipeptide was prepared in the same way as Boc-Phe-D-Ala-OMe was prepared in Example 2D described above. The peptide was obtained in a 90% yield.

F. Fmoc-Ala-Gly-OMe

Thionyl chloride (4.7 ml, 64.2 mM) was added to a suspension of Fmoc-Ala (4.0 g, 12.85 mM) in chloroform (20 ml) and dimethylformamide (DMF, 0.1 ml). The mixture was refluxed for 1.0 hour. The resulting clear solution was concentrated, treated with dichloromethane (DCM, 3×10 ml) and concentrated each time to give acid chloride as a solid.

The solid was dissolved in DCM (50 ml) and cooled under an ice bath. Gly-OMe.HCl (1.93 g, 15.4 mM) and propylene oxide (2.26 g, 39 mM) were sequentially added. The reaction mixture was stirred under ice bath for 2–3 hours and then for 12–18 hours at room temperature. A 5% bicarbonate solution (30 ml) was added and the mixture stirred for 15 minutes. The organic lower layer was separated, diluted with DCM (25 ml), and washed with a sodium chloride solution (30 ml). The organic solution was then dried with sodium sulfate and concentrated to a solid.

The solid was crystallized from ethyl acetate/heptane to give the dipeptide as a white solid yield of 2.8 g (57%) with amp of 158°–159° C. NMR and mass spectral data were consistent with the structure.

What is claimed is:

1. A process of synthesizing a peptide comprising the steps of:

a) reacting an N-α-amino-Boc-protected amino acid residue with an N-α-amino unprotected amino acid residue to form a peptide having an α-amino-Boc-protected amino terminus;

b) reacting the formed peptide with an acid solution to remove the α-amino-Boc protecting group from the amino terminus of the peptide: and c) neutralizing the acid with an alkylene oxide solution.

2. The process of claim 1 wherein the N-α-amino unprotected amino acid residue is linked via an amide bond at its α-carboxyl group to one or more amino acid residues.

3. The process of claim 1 wherein synthesizing occurs in a solution phase.

4. The process of claim 1 wherein synthesizing occurs in a solid phase.

5. The process of claim 1 wherein the acid solution includes an acid selected from the group consisting of: trifluoroacetic acid, hydrochloric acid, sulfuric acid or methanesulfonic acid.

6. The process of claim 5 wherein the acid is hydrochloric acid.

7. The process of claim 6 wherein the acid solution includes tetrahydrofuran.

8. The process of claim 1 wherein the alkylene oxide solution is propylene oxide.

9. The process of claim 8 wherein the alkylene oxide solution includes a solvent selected from the group consisting of: dimethylformamide or N-methyl-2-pyrrolidine.

* * * * *